(12) United States Patent
Kuyler et al.

(10) Patent No.: US 11,020,154 B2
(45) Date of Patent: Jun. 1, 2021

(54) SURGICAL INSTRUMENT AND METHODS OF USE

(71) Applicant: Warsaw Orthopedic, Inc., Warsaw, IN (US)

(72) Inventors: Adriaan J. Kuyler, Germantown, TN (US); Benjamin D. Cowan, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/395,840

(22) Filed: Apr. 26, 2019

(65) Prior Publication Data
US 2020/0337742 A1 Oct. 29, 2020

(51) Int. Cl.
*A61B 17/70* (2006.01)

(52) U.S. Cl.
CPC ...... *A61B 17/7082* (2013.01); *A61B 17/7001* (2013.01)

(58) Field of Classification Search
CPC ............ A61B 17/7001; A61B 17/7005; A61B 17/7002; A61B 17/7004; A61B 17/7007; A61B 17/7008; A61B 17/7076; A61B 17/7077; A61B 17/7079; A61B 17/708; A61B 17/7082; A61B 17/8875; A61B 17/8877; A61B 17/888; A61B 17/8883; A61B 17/8886; A61B 17/8891; A61B 17/1686; A61B 17/863; A61B 17/8863; A61B 17/8635; A61B 17/8645; A61B 17/8685; A61B 17/746; A61B 17/8869; A61B 17/742; A61B 17/744; A61B 17/8625; A61B 17/861; A61B 2017/0648; A61B 2017/0646; A61B 2017/90

USPC ...... 606/65, 79, 104, 96, 99, 86 A, 300–328
See application file for complete search history.

(56) References Cited

U.S. PATENT DOCUMENTS

| 5,423,819 A | 6/1995 | Small et al. |
| 5,797,914 A | 8/1998 | Leibinger |
| 5,964,768 A * | 10/1999 | Huebner ............ A61B 17/1686 411/115 |
| 6,743,233 B1 | 6/2004 | Baldwin et al. |
| 7,819,905 B2 | 10/2010 | Newcomb et al. |
| 7,951,198 B2 * | 5/2011 | Sucec ................. A61B 17/562 606/300 |
| 8,118,849 B2 | 2/2012 | Wahl et al. |
| 8,500,748 B2 * | 8/2013 | Yu ........................ A61B 17/861 606/99 |
| 8,529,608 B2 | 9/2013 | Terrill et al. |

(Continued)

FOREIGN PATENT DOCUMENTS

EP 0654249 B1 5/1995

OTHER PUBLICATIONS

International Search Reprt, Korean Patent Office, PCT/US2020/029680, dated Aug. 5, 2020.

*Primary Examiner* — Pedro Philogene
(74) *Attorney, Agent, or Firm* — Sorell, Lenna & Schmidt, LLP

(57) ABSTRACT

A spinal implant includes a distal portion configured for penetrating tissue. A proximal portion includes a drive surface, a guide surface and a retention surface. The surfaces being disposed in a serial configuration. The retention surface is engageable with a surface of a surgical instrument to define a retention interface. Instruments, systems, constructs and methods are disclosed.

20 Claims, 9 Drawing Sheets

(56) References Cited

U.S. PATENT DOCUMENTS

| | | | |
|---|---|---|---|
| 8,668,725 B2 | 3/2014 | Smisson, III et al. | |
| 8,747,472 B2 * | 6/2014 | Ainsworth | A61B 17/70 606/105 |
| 8,828,067 B2 | 9/2014 | Tipirneni et al. | |
| 9,421,005 B2 * | 8/2016 | Bonutti | A61B 17/7058 |
| 9,545,275 B2 | 1/2017 | Cawley et al. | |
| 9,724,149 B2 * | 8/2017 | Trieu | A61B 17/8875 |
| 9,924,972 B2 | 3/2018 | Yue | |
| 10,064,707 B2 * | 9/2018 | Zadeh | A61C 8/006 |
| 2009/0198291 A1 | 8/2009 | Foley et al. | |
| 2009/0326545 A1 | 12/2009 | Schaffhausen | |
| 2011/0111369 A1 * | 5/2011 | Laster | A61B 17/0401 433/174 |
| 2011/0306984 A1 | 12/2011 | Sasing | |
| 2014/0005731 A1 | 1/2014 | Biedermann et al. | |
| 2018/0140331 A1 | 5/2018 | Biedermann et al. | |
| 2019/0021846 A1 * | 1/2019 | Williams | A61F 2/0811 |

\* cited by examiner

SURGICAL INSTRUMENT AND METHODS OF USE

TECHNICAL FIELD

The present disclosure generally relates to medical devices for the treatment of musculoskeletal disorders, and more particularly to a surgical system for delivering and/or fastening implants with a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. Surgical instruments are employed, for example, to engage the fasteners for attachment to the exterior of two or more vertebral members. This disclosure describes an improvement over these prior technologies.

SUMMARY

In one embodiment, a spinal implant instrument is provided. The spinal implant includes a distal portion configured for penetrating tissue. A proximal portion includes a drive surface, a guide surface and a retention surface. The surfaces being disposed in a serial configuration. The retention surface is engageable with a surface of a surgical instrument to define a retention interface. In some embodiments, systems instruments, systems, constructs and methods are disclosed.

In one embodiment, a surgical system is provided. The surgical system includes a surgical instrument including a drive surface and a retention surface. A spinal implant includes a drive surface and a retention surface. At least one of the retention surfaces is tapered, and the retention surfaces are engageable to define a retention interface.

In one embodiment, a surgical system is provided. The surgical system includes a driver including a drive surface and a retention surface. A bone screw including a threaded shaft and a head having a drive surface, a guide surface and a retention surface. The surfaces are disposed in a serial configuration. At least one of the retention surfaces is tapered, and the retention surfaces are engageable to retain the implant with the surgical instrument.

BRIEF DESCRIPTION OF THE DRAWINGS

The present disclosure will become more readily apparent from the specific description accompanied by the following drawings, in which.

DETAILED DESCRIPTION

Figure 1:
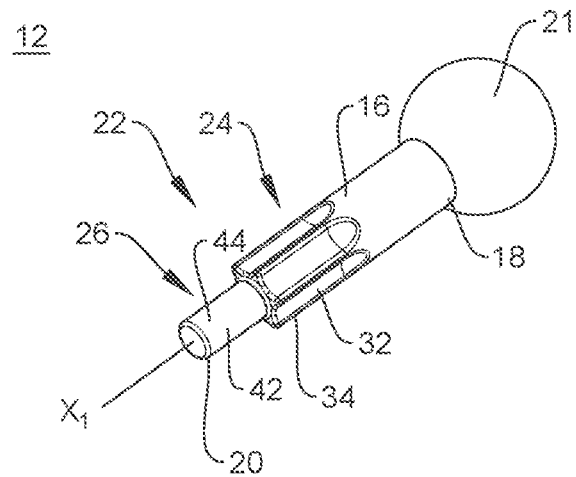
FIG. 1 is a perspective view of components of one embodiment of a spinal implant system in accordance with the principles of the present disclosure.

The exemplary embodiments of a surgical system are discussed in terms of medical devices for the treatment of musculoskeletal disorders and more particularly, in terms of a surgical system for delivering and/or fastening implants with a surgical site and a method for treating a spine. In some embodiments, the surgical system includes a surgical instrument, such as, for example, an implant driver and a spinal implant, such as, for example, a bone screw In some embodiments, the surgical system includes a surgical instrument including a drive surface and a retention surface. In some embodiments, the surgical system includes a spinal implant including a drive surface and a retention surface. In some embodiments, at least one of the retention surfaces is tapered, and the retention surfaces are engageable to define a retention interface. In some embodiments, at least one of the retention surfaces is cylindrical, and the retention surfaces are engageable to define a retention interface. In some embodiments, rotational engagement is facilitated due to the retention surfaces holding the surgical instrument axially independently of the drive geometry.

In some embodiments, the spinal implant includes a distal portion configured for penetrating tissue. In some embodiments, the spinal implant includes proximal portion having a drive surface, a guide surface and a retention surface. In some embodiments, the surfaces are disposed in a serial configuration. In some embodiments, the retention surface is engageable with a surface of a surgical instrument to define a retention interface.

In some embodiments, the surgical system may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, spinal implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 includes a surgical instrument, such as, for example, a driver 12 engageable with a spinal implant, such as, for example, a bone screw 14, as shown in FIGS. 1-4. In some embodiments, driver 12 may be utilized with other devices, such as, for example, set screws and/or interbody cages.

Driver 12 includes a member, such as, for example, an elongated shaft 16. Shaft 16 extends between an end, such as, for example, a proximal end 18 and an end, such as, for example, a distal end 20. Shaft 16 has a cylindrical cross sectional configuration between ends 18, 20 and includes a diameter D1. In some embodiments, a portion of shaft 16 may have alternate cross section configurations, such as, for example, oval, oblong, triangular, square, polygonal, irregular, uniform, non-uniform, offset, staggered, and/or tapered. Shaft 16 defines a longitudinal axis X1.

In some embodiments, end 18 is configured for engagement and connection with a handle 21, which is configured to facilitate manipulation of driver 12. In some embodiments, the handle may be disposed at alternate orientations relative to shaft 16, such as, for example, transverse, perpendicular and/or other angular orientations such as acute or obtuse. In some embodiments, end 18 is configured for engagement and connection with an adaptor, extension and/or other connection to facilitate manipulation of driver 12.

In some embodiments, end 18 includes a tool engagement surface (not shown) configured to engage an actuator, such as, for example, a surgical instrument and/or hand drill to rotate end 20 in a first direction and/or an opposing second direction, such as, for example, clockwise and counter-clockwise directions. In some embodiments, end 18 may include an interchangeable driving handle removably connected to end 18 such that torque applied manually or by a motorized actuator to the handle is transmitted to shaft 16.

In some embodiments, end 18 is configured to engage an actuator, such as, for example, a motorized actuator, such as, for example, a powered drill (not shown). In some embodiments, the motorized actuator includes a mating connector, such as, for example, a chuck. In some embodiments, the chuck includes a socket that is configured to mate with end 18. In some embodiments, the motorized actuator includes an electric motor, such as, for example, an electric drill motor that is connected to a power source, such as, for example, a battery and/or AC source, for rotating end 20. In one embodiment, the motorized actuator may be pneumatic or hydraulic.

Figure 2:
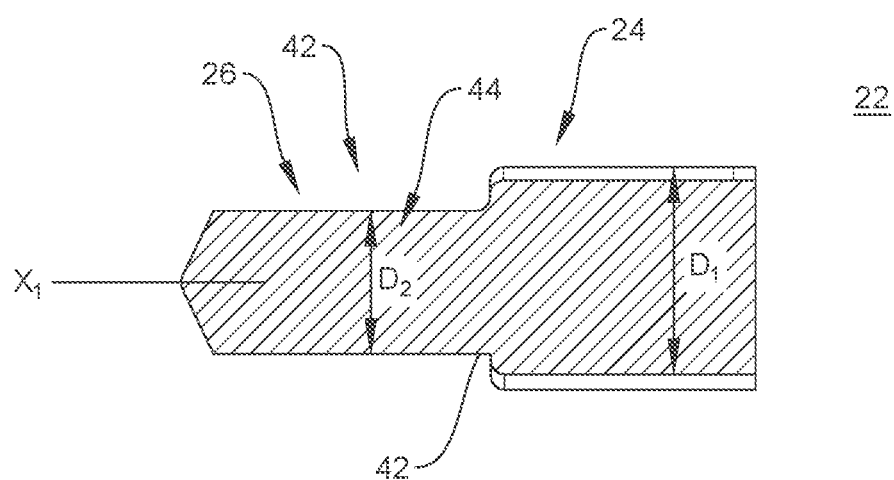
FIG. 2 is a side cross section view of the components shown in FIG. 1.
Figure 3:
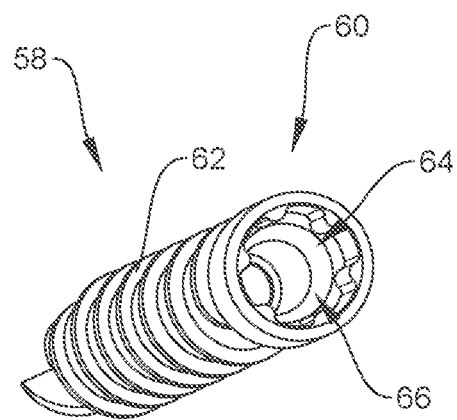
FIG. 3 is a perspective view of components of one embodiment of a spinal implant system in accordance with the principles of the present disclosure.

End 20 includes an engagement portion 22. Portion 22 is configured for engagement with bone screw 14, as described herein. Portion 22 includes a drive portion 24 and a retention portion 26. Portions 24, 26 are disposed in a serial configuration along axis X1, as shown in FIG. 2.

Portion 24 includes a plurality of spaced apart lobes 32 disposed circumferentially about portion 26, as shown in FIG. 1. Lobes 32 includes a hexalobe configuration. In some embodiments, Portion 24 may have alternate configurations, such as, for example, thread form, triangular, square, polygonal, star, torx, irregular, uniform, non-uniform, offset, staggered, and/or tapered.

Each lobe 32 includes a drive surface 34 and a trailing surface 36 that is spaced apart from drive surface 34. In some embodiments, all or a portion of lobe 32 may include various configurations and/or be disposed in various orientations, such as, for example, angular, arcuate, undulating, series, parallel, offset and/or staggered. Drive surface 34 is configured to contact a portion of a socket 66 of bone screw 14, as described herein, at a drive interface 38 to drive, torque, insert or otherwise rotate bone screw 14.

Portion 24 includes a distal face 40. Distal face 40 includes a flat or even surface. In some embodiments, distal face 40 may have various surface configurations, such as, for example, rough, threaded, arcuate, undulating, porous, semi-porous, dimpled, polished and/or textured.

Portion 26 includes an extension 42 extending from distal face 40. In some embodiments, extension 42 is monolithically formed with distal face 40. In some embodiments, extension 42 is integrally connected with distal face 40. In some embodiments, extension 42 is attachable with distal face 40 with fastening elements and/or instruments.

Extension 42 includes a cylindrical cross-sectional configuration, as shown in FIG. 2. some embodiments, all or only a portion of extension 42 may have alternate cross section configurations, such as, for example, oval, oblong, triangular, square, polygonal, irregular, uniform, non-uniform, offset, staggered, and/or tapered.

Extension 42 includes a diameter D2. Diameter D2 is less than diameter D1. Extension 42 includes a surface 44 that facilitates engaging and retaining of driver 12 with bone screw 14. Surface 44 is configured to contact a portion of bone screw 14 at a retention interface 46, as described herein. Retention interface 46 provides for a connection between extension 42 and bone screw 14 that is independent of the geometry of driver 12 and socket 66. For example, as bone screw 14 is driven into the bone, slight distortions occur under a normal driving force, retention interface 46 resists and/or prevents driver 12 from disengaging from bone screw 14 unexpectedly. In some embodiments, retention interface 46 is configured to cause wear on a surface of bone screw 14 rather than driver 12 providing for a more durable connection. Retention interface 46 is configured to resist and/or prevent stripping of socket 66 by distributing the torque load across drive interface 38 and retention interface 46. In some embodiments, retention interface 46 provides a configuration that resists and/or prevents toggle between driver 12 and bone screw 14.

Figure 4:
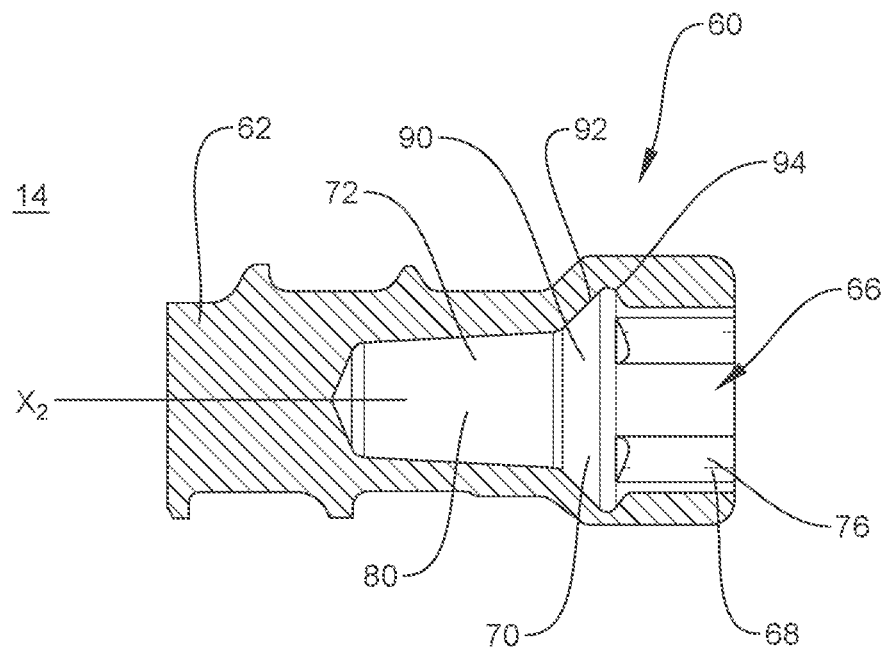
FIG. 4 is a side cross section view of the components shown in FIG. 3.

Bone screw 14 extends along an axis X2, as shown in FIG. 4. Bone screw 14 shown in FIG. 3 includes a distal portion 58 and a proximal portion 60. Distal portion 58 includes a shaft 62 configured to penetrate tissue, such as, for example, bone. Shaft 62 includes a thread form on an outer surface thereof. In some embodiments, the thread form may extend such that shaft 62 is threaded along the entire length thereof. In some embodiments, all or only a portion of shaft 62 may have various surface configurations, such as, for example, rough, threaded, arcuate, undulating, porous, semi-porous, dimpled, polished and/or textured.

Proximal portion 60 includes a socket 66. Socket 66 defines recesses 76 configured for disposal of lobes 32. In some embodiments, recesses 76 includes a hexalobe configuration. In some embodiments, recesses 76 may have alternate configurations, such as, for example, thread form, triangular, square, polygonal, star, torx, irregular, uniform, non-uniform, offset, staggered, and/or tapered.

Figure 5:
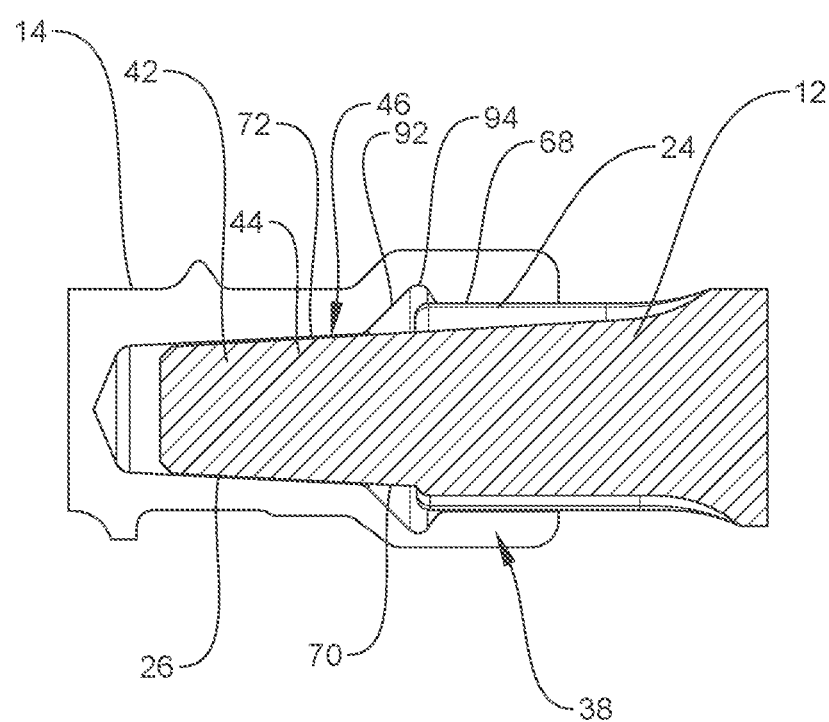
FIG. 5 is a side cross section view of components of one embodiment of a spinal implant system in accordance with the principles of the present disclosure.

Each recess 76 includes a drive surface 68 configured for engagement with drive surface 34 at drive interface 38, as shown in FIG. 5, causing drive surface 34 to drive, torque, insert or otherwise rotate bone screw 14 by applying a force to drive surface 68.

Figure 7:
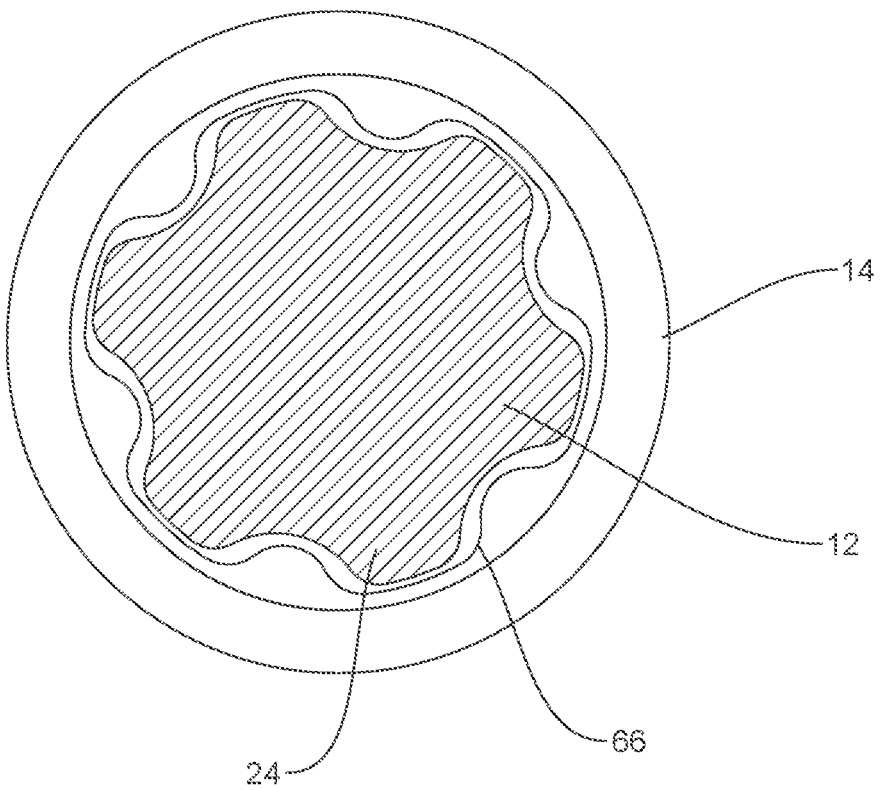
FIG. 7 is a top cross section view of components of one embodiment of a spinal implant system in accordance with the principles of the present disclosure.

Surface 72 defines a cavity 80 configured for disposal of extension 42. Cavity 80 includes a tapered configuration, as shown in FIG. 4. Cavity 80 tapers from proximal portion 60 towards distal portion 58. Surface 44 of extension 42 is configured to contact surface 72 at retention interface 46, as described herein and shown in FIG. 5. Retention interface 46 provides for a connection between driver 12 and bone screw 14 that is independent of the geometry of driver 12 and socket 66. Retention interface 46 is configured to facilitate engagement of driver 12 with bone screw 14 during a final tightening check before closing the surgical site. In some embodiments, portion 24 is not wedged rotationally into socket 66, as shown in FIG. 7. In some embodiments, this facilitates disengagement of driver 12 from bone screw 14 by requiring only a slight wiggle of driver 12 and rotating counter-clockwise to clockwise and back to disengage driver 12 from bone screw 14 without requiring any additional force.

A surface 70 is disposed between socket 66 and cavity 80, as shown in FIG. 4. Surface 70 defines a cavity 90. Surface 70 includes an undercut, such as, for example, a ramp 92. Ramp 92 defines a cone shaped cross section of cavity 90, as shown in FIG. 4. Ramp 92 is oriented to decline from proximal portion 60 towards distal portion 58. Ramp 92 facilitates aligning and/or guiding extension 42 into cavity 80. In some embodiments, surface 70 is configured to facilitate retaining driver 12 with bone screw 14. Surface 70 defines a gap 94 having an angled surface configured to direct extension 34 into cavity 90. Gap 94 facilitates manipulation and angling of extension 45 into cavity 80.

For example, extension 42 is guided into cavity 90. Extension 42 having the cylindrical shape, as described herein, is translated into cavity 90 causing surface 44 to contact surface 72 of tapered cavity 80. An interference fit and/or friction fit is formed between surface 44 and surface 72 at retention interface 46 retaining driver 12 with bone screw 14.

In assembly, operation and use, surgical system 10, similar to surgical systems and methods described herein, is employed with a surgical procedure for treatment of a spinal disorder affecting a section of a spine of a patient, as discussed herein. For example, surgical system 10 can be used with a surgical procedure for treatment of a condition or injury of an affected section of the spine including vertebrae (not shown). In some embodiments, one or all of the components of surgical system 10 can be delivered or implanted as a pre-assembled device or can be assembled in situ. Surgical system 10 may be completely or partially revised, removed or replaced.

For example, surgical system 10 can be employed with a surgical treatment of an applicable condition or injury of an affected section of a spinal column and adjacent areas within a body, such as, for example, vertebrae. In some embodiments, surgical system 10 may be employed with one or a plurality of vertebra. To treat a selected section of the vertebrae, a medical practitioner obtains access to a surgical site including the vertebrae in any appropriate manner, such as through incision and retraction of tissues. In some embodiments, surgical system 10 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of surgical system 10. A preparation instrument (not shown) can be employed to prepare tissue surfaces of the vertebrae, as well as for aspiration and irrigation of a surgical region.

Pilot holes or the like are made in selected vertebra of the vertebrae for receiving bone screws 14. Surgical system 10 is disposed adjacent the vertebrae at a surgical site and the components of surgical system 10 including driver 12, are manipulable to drive, torque, insert or otherwise connect bone screws 14 to the vertebrae.

Figure 8:
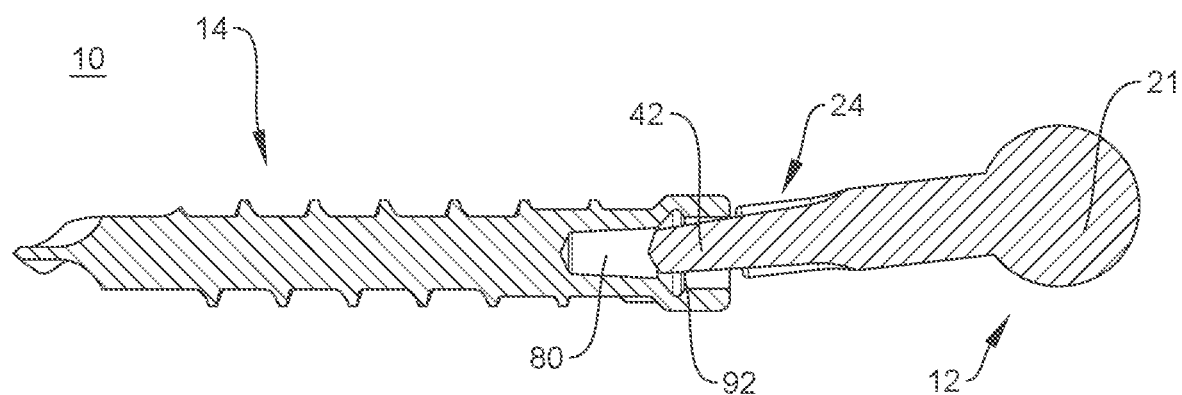
FIG. 8 is a side cross section view of components of one embodiment of a spinal implant system in accordance with the principles of the present disclosure.
Figure 9:
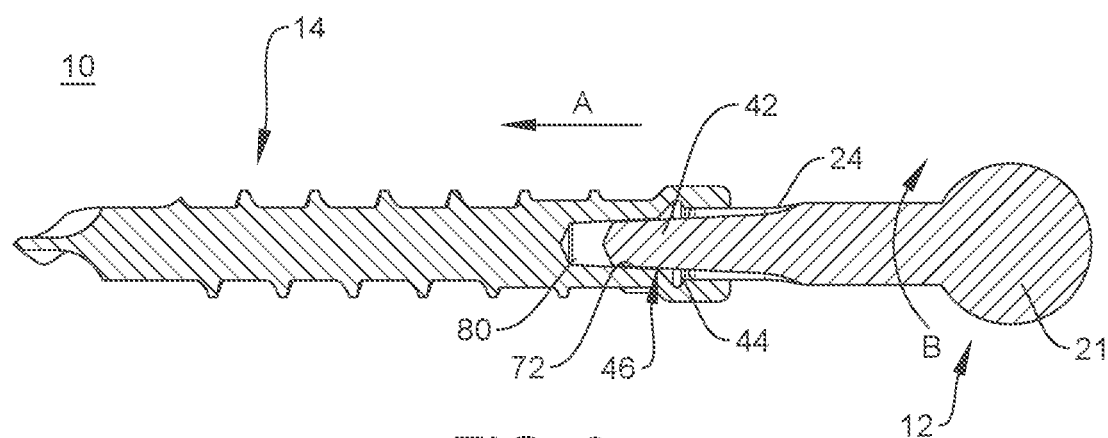
FIG. 9 is a side cross section view of components of one embodiment of a spinal implant system in accordance with the principles of the present disclosure.

As shown in FIGS. 8 and 9, driver 12 is manipulated relative to bone screw 14 such that extension 42 is disposed with cavity 90. Extension 42 contacts surface 70 of ramp 92. Ramp 92 aligns and distally directs extension 42 to axially translate extension 42, in a direction shown by arrow A in FIG. 9, into cavity 80. As driver 12 translates, extension 42 translates into cavity 80 and an interference fit and/or friction fit is formed between surface 44 and surface 72 at retention interface 46 retaining driver 12 with bone screw 14.

Figure 6:
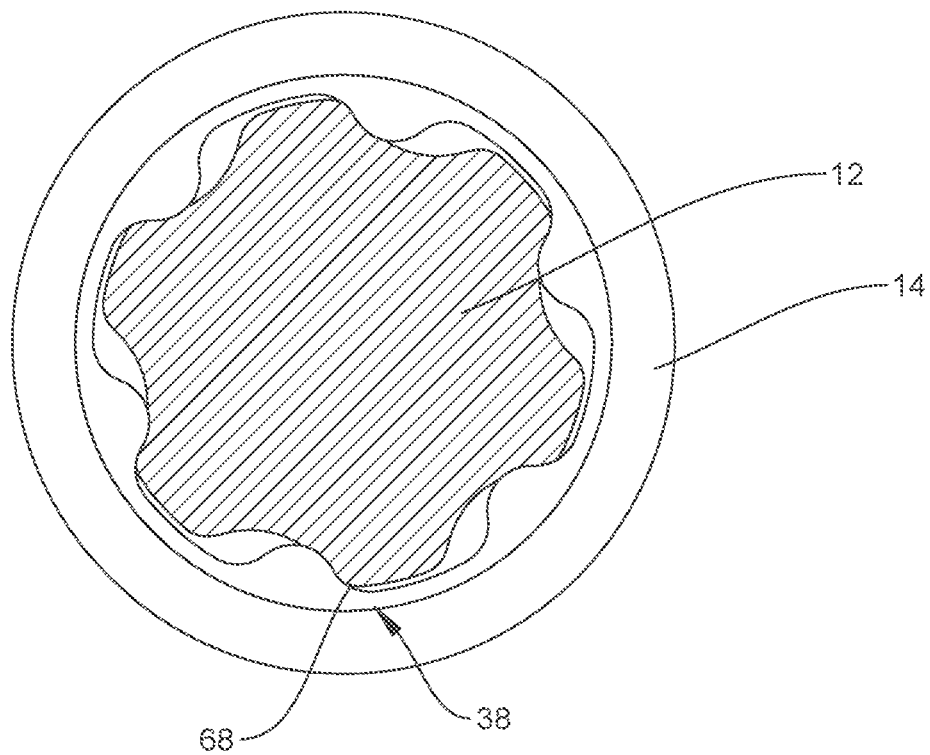
FIG. 6 is a top cross section view of components of one embodiment of a spinal implant system in accordance with the principles of the present disclosure.

Portion 24 is disposed with socket 66 such that lobes 32 are disposed within recesses 74, as shown in FIG. 7. Driver 12 is rotated, as shown by arrow B in FIG. 9, causing drive surface 34 to contact drive surface 68 of socket 66, as shown in FIG. 6, to provide a driving torque to fasten bone screw 14 with vertebrae.

Interfaces 38, 46 of driver 12 with bone screw 14 resist and/or prevent toggle between driver 12 and bone screw 14. Disengagement of driver 12 is facilitated by requiring only a slight wiggle of driver 12 and rotating counter-clockwise to clockwise and back to disengage driver 12 from bone screw 14 without requiring any additional force.

Once access to the surgical site is obtained, the particular surgical procedure is performed. The components of surgical system 10, including bone screw 14 are employed to augment the surgical treatment. For example, bone screw 14 may be inserted into bone or other tissue with driver 12, for example, via clockwise or counterclockwise rotation. Bone screw 14 may be delivered, introduced, inserted and/or removed from bone or other tissue with driver 12.

Surgical system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, surgical system 10 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, such as, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implant components of surgical system 10 are removed from the surgical site and the incision is closed.

In one embodiment, as shown in FIGS. 10-13, surgical system 10, similar to the systems and methods described above with regard to FIGS. 1-7, includes a driver 112, similar to driver 12 described herein. Driver 12 includes an elongated shaft 116, similar to shaft 16 described herein.

Shaft 116 includes an engagement portion 122, similar to portion 22 as described herein. Portion 122 is configured for engagement with a bone screw 114, similar to bone screw 14 described herein. Portion 122 includes a drive portion 124 and a retention portion 126.

Portion 124 includes a plurality of spaced apart lobes 132, similar to lobes 32 disposed circumferentially about portion 126. Each lobe 132 includes a drive surface 134, similar to drive surface 34 as described herein. Drive surface 134 is configured to contact a portion of a socket 166 of bone screw 114, as described herein, at a drive interface 138 to drive, torque, insert or otherwise rotate bone screw 114.

Figure 10:
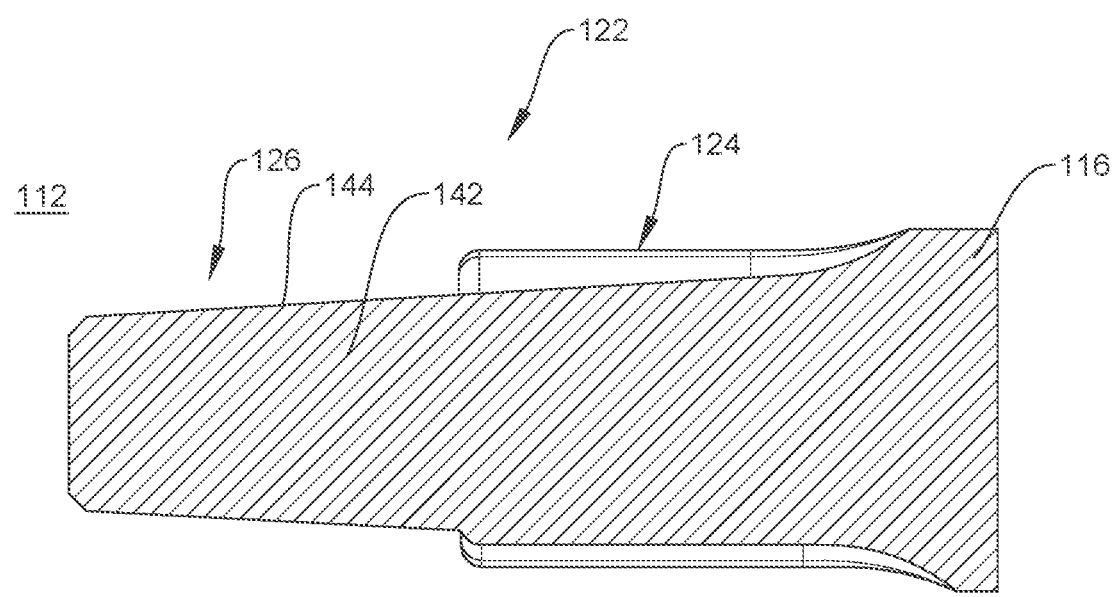
FIG. 10 is a side cross section view of components of one embodiment of a spinal implant system in accordance with the principles of the present disclosure.

Shaft 116 includes an extension 142, similar to extension 42 as described herein. Extension 142 includes a tapered cross-sectional configuration, as shown in FIG. 10. Extension tapers from a proximal portion towards a distal portion. Extension 142 includes a surface 144 that facilitates engaging and retaining of driver 112 with bone screw 114. Surface 144 is configured to contact a portion of bone screw 114 at a retention interface 146, as described herein.

Bone screw 114 includes a distal portion 158 and a proximal portion 160. Distal portion 158 includes a shaft 162 configured to penetrate tissue, such as, for example, bone, as described herein. Shaft 162 includes a thread form on an outer surface thereof.

Proximal portion 160 includes a socket 166. Socket 166 defines recesses 176 configured for disposal of lobes 132, as described herein. Each recess 176 includes a drive surface 168 configured for engagement with drive surface 134 at drive interface 138, as described herein, causing drive surface 134 to drive, torque, insert or otherwise rotate bone screw 114 by applying a force to drive surface 168.

Figure 11:
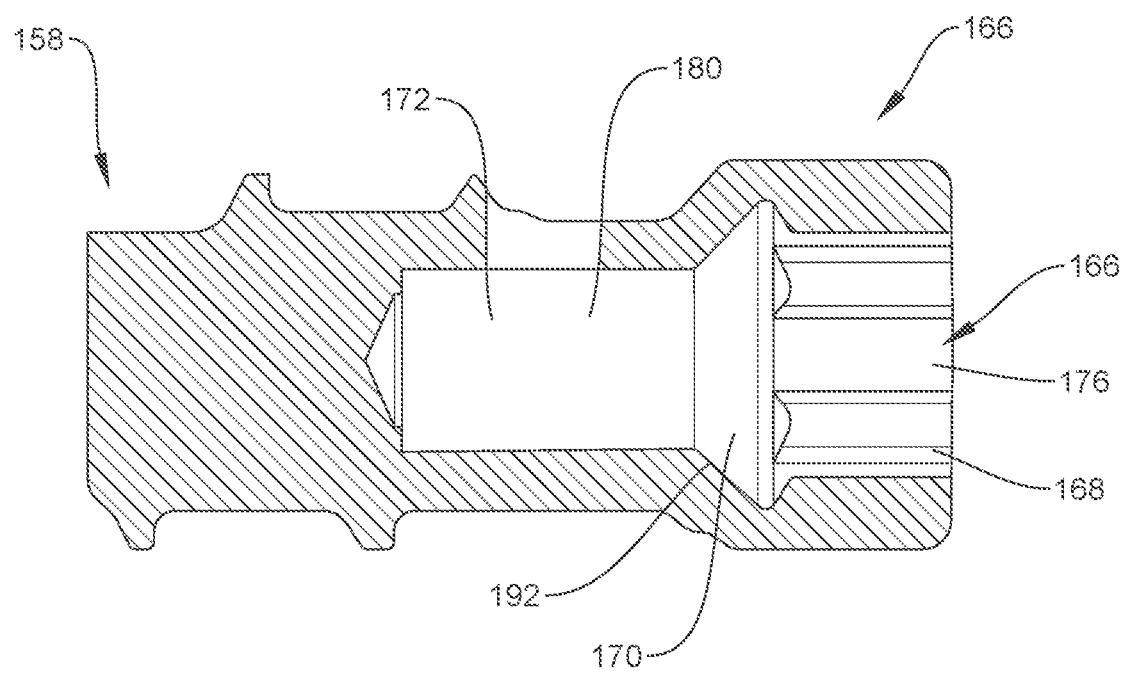
FIG. 11 is a side cross section view of components of one embodiment of a spinal implant system in accordance with the principles of the present disclosure.
Figure 12:
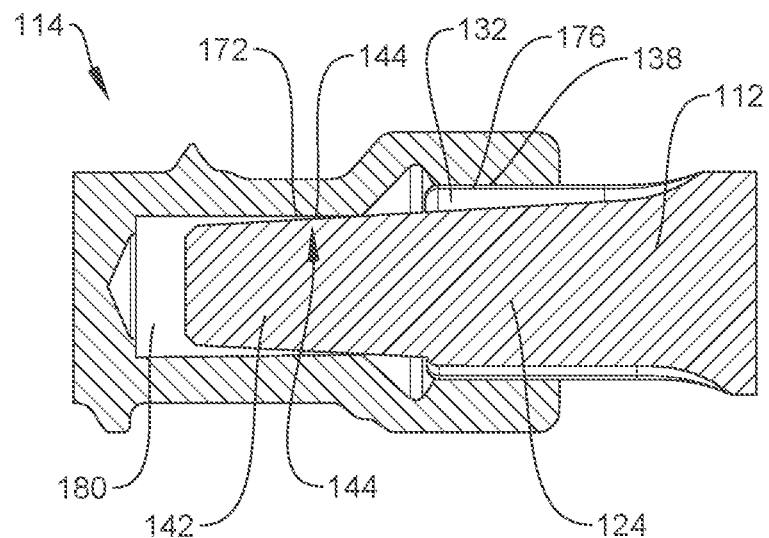
FIG. 12 is a side cross section view of components of one embodiment of a spinal implant system in accordance with the principles of the present disclosure.
Figure 13:
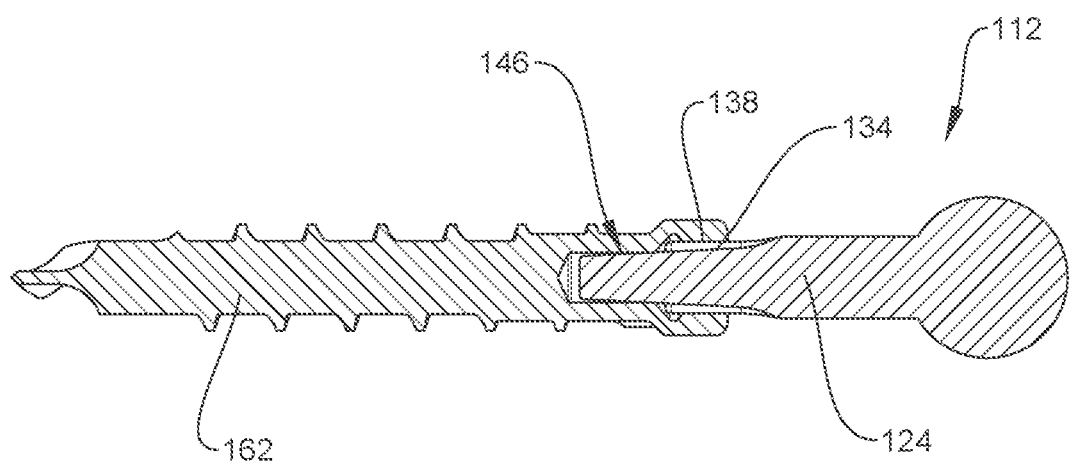
FIG. 13 is a side cross section view of components of one embodiment of a spinal implant system in accordance with the principles of the present disclosure.

Surface 172 defines a cavity 180 configured for disposal of extension 142, as described herein. Cavity 180 includes a cylindrical configuration, as shown in FIG. 11. Surface 144 of extension 142 is configured to contact surface 172 at retention interface 146, as described herein and shown in FIG. 12.

A surface 170 defines a cavity 190. Surface 170 includes an undercut, such as, for example, a ramp 192. Ramp 192 defines a cone shaped cross section of cavity 190, as shown in FIG. 11. Ramp 192 is oriented to decline from proximal portion 160 towards distal portion 158. Ramp 192 facilitates aligning and/or guiding extension 142 into cavity 180, as described herein.

In one embodiment, as shown in FIGS. 14-17, surgical system 10, similar to the systems and methods described above with regard to FIGS. 1-7, includes a driver 212, similar to driver 12 described herein. Driver 212 includes an elongated shaft 216, similar to shaft 16 described herein.

Shaft 216 includes an engagement portion 222, similar to portion 22 as described herein. Portion 222 is configured for engagement with a bone screw 214, similar to bone screw 14 described herein. Portion 222 includes a drive portion 224 and a retention portion 226.

Portion 224 includes a plurality of spaced apart lobes 232, similar to lobes 32 disposed circumferentially about portion 226. Each lobe includes a drive surface 234, similar to drive surface 34 as described herein. Drive surface 234 is configured to contact a portion of a socket 266 of bone screw 214, as described herein, at a drive interface 238 to drive, torque, insert or otherwise rotate bone screw 214.

Figure 14:
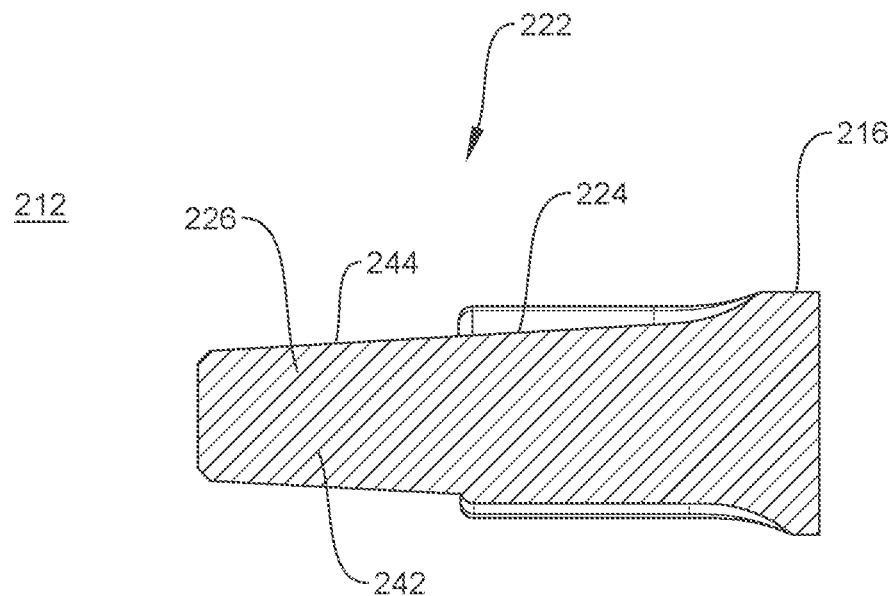
FIG. 14 is a side cross section view of components of one embodiment of a spinal implant system in accordance with the principles of the present disclosure.

Shaft 216 includes an extension 242, similar to extension 42 as described herein. Extension 242 includes a tapered cross-sectional configuration, as shown in FIG. 14. Extension tapers from a proximal portion towards a distal portion. Extension 242 includes a surface 244 that facilitates engaging and retaining of driver 212 with bone screw 214. Surface 244 is configured to contact a portion of bone screw 214 at a retention interface 246, as described herein.

Bone screw 214 includes a distal portion 258 and a proximal portion 260. Distal portion 258 includes a shaft 262 configured to penetrate tissue, such as, for example, bone, as described herein. Shaft 262 includes a thread form on an outer surface thereof.

Proximal portion 260 includes socket 266. Socket 266 defines recesses 276 configured for disposal of lobes 232, as described herein. Each recess 276 includes a drive surface 268 configured for engagement with drive surface 234 at drive interface 238, as described herein, causing drive surface 234 to drive, torque, insert or otherwise rotate bone screw 214 by applying a force to drive surface 268.

Figure 15:
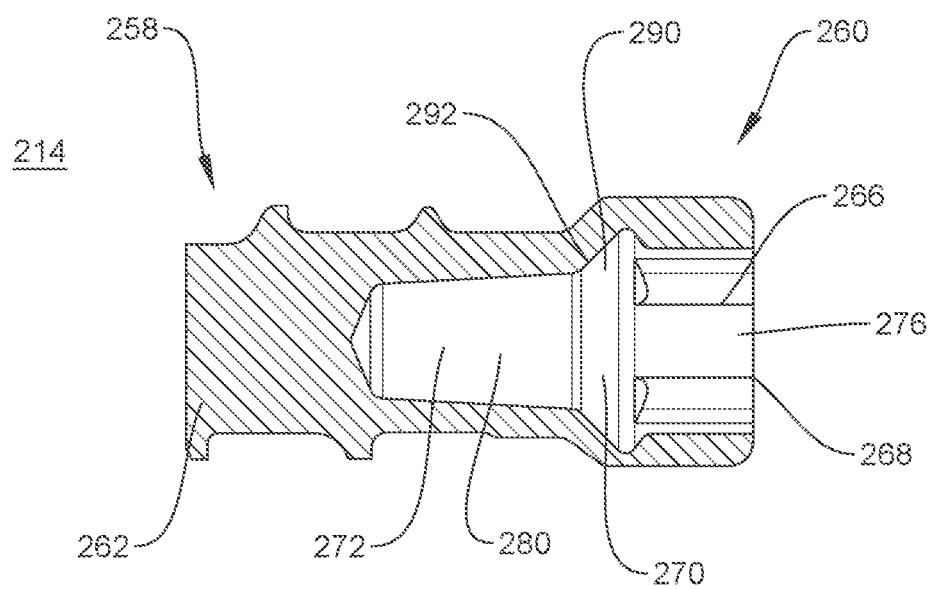
FIG. 15 is a side cross section view of components of one embodiment of a spinal implant system in accordance with the principles of the present disclosure.
Figure 16:
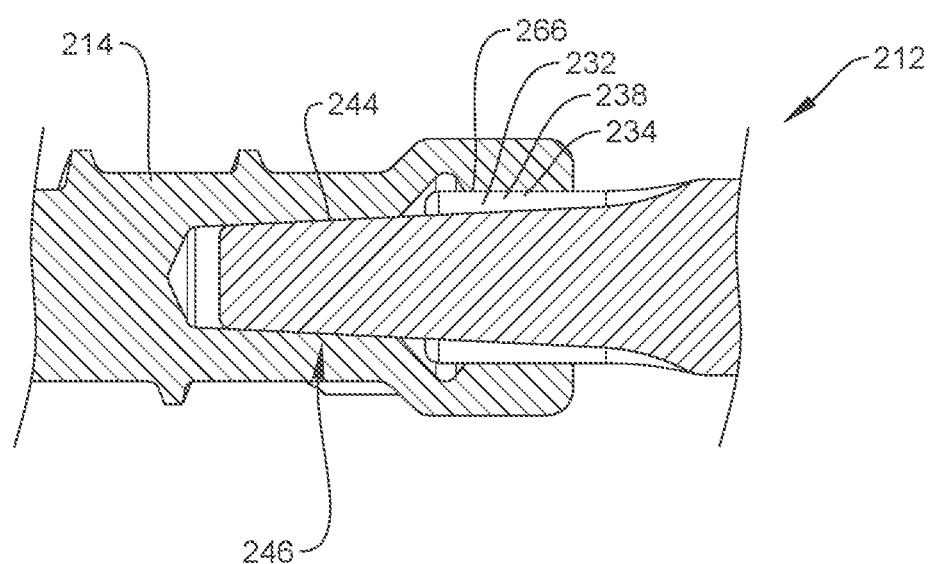
FIG. 16 is a side cross section view of components of one embodiment of a spinal implant system in accordance with the principles of the present disclosure.
Figure 17:
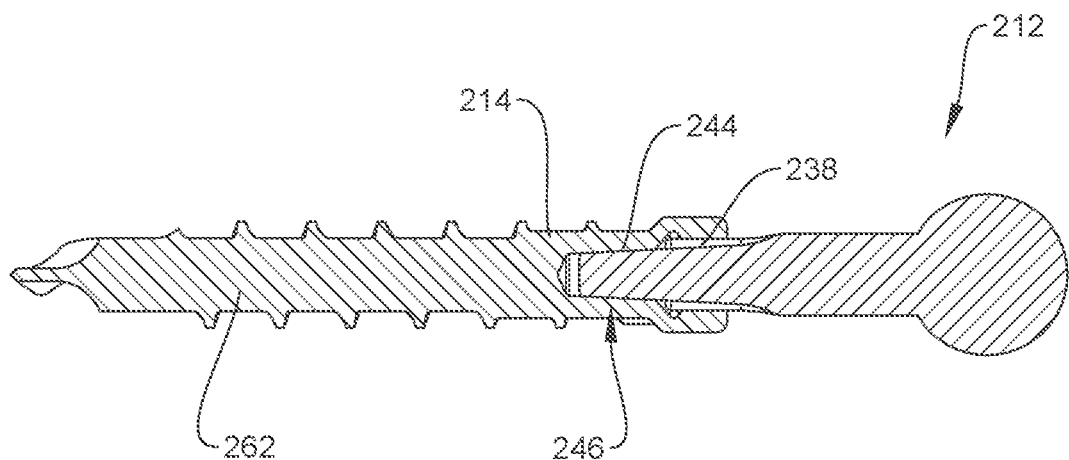
FIG. 17 is a side cross section view of components of one embodiment of a spinal implant system in accordance with the principles of the present disclosure.

Surface 272 defines a cavity 280 configured for disposal of extension 242, as described herein. Cavity 280 includes a tapered configuration, as shown in FIG. 15. Cavity 280 tapers from proximal end 260 to distal end 258. Surface 244 of extension 242 is configured to contact surface 272 at retention interface 246, as described herein and shown in FIG. 16.

A surface 270 defines a cavity 290. Surface 270 includes an undercut, such as, for example, a ramp 292. Ramp 292 defines a cone shaped cross section of cavity 190, as shown in FIG. 14. Ramp 292 is oriented to decline from proximal portion 260 towards distal portion 258. Ramp 292 facilitates aligning and/or guiding extension 242 into cavity 280, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
 a distal portion configured for penetrating tissue;
 a proximal portion including a drive surface, a guide surface and a retention surface, the surfaces defining a socket, the drive surface defining a first cavity of the socket, the guide surface defining a second cavity of the socket and the retention surface defining a third cavity of the socket, the surfaces being disposed in a serial configuration, an interface between the drive surface and the guide surface being arcuate and defining a gap, the gap defining a maximum diameter of the socket,
 wherein the retention surface is engageable with a surface of a surgical instrument to define a retention interface.

2. A spinal implant as recited in claim 1, wherein the retention surface and the surface of the surgical instrument form a friction fit.

3. A spinal implant as recited in claim 1, wherein the third cavity includes a tapered configuration.

4. A spinal implant as recited in claim 1, wherein the third cavity includes a cylindrical configuration.

5. A spinal implant as recited in claim 1, wherein second cavity is disposed between the drive surface and the retention surface.

6. A spinal implant as recited in claim 5, wherein the second cavity includes a cone shaped cross section configured to align and direct the surgical instrument into engagement with the retention surface.

7. A spinal implant as recited in claim 1, wherein the gap has an angled surface configured to direct the surface of the surgical instrument into engagement with the retention surface.

8. A spinal implant as recited in claim 1, wherein the guide surface includes an undercut.

9. A spinal implant as recited in claim 1, wherein the drive surface includes a hexalobe geometry configured for engagement with a drive surface of the surgical instrument.

10. A spinal implant as recited in claim 1, wherein the surface of the surgical instrument includes a tapered configuration.

11. A spinal implant as recited in claim 1, wherein the surface of the surgical instrument includes a cylindrical configuration.

12. A surgical system comprising:
 a surgical instrument including a drive surface and a retention surface; and
 a spinal implant including a drive surface, a guide surface and a retention surface, the surfaces of the spinal implant defining a socket, the drive surface of the spinal implant defining a first cavity of the socket, the guide surface defining a second cavity of the socket and the retention surface of the spinal implant defining a third cavity of the socket, an interface between the drive surface of the spinal implant and the guide surface being arcuate and defining a maximum diameter of the socket;
 wherein at least one of the retention surfaces is tapered, and the retention surfaces are engageable to define a retention interface.

13. A surgical system as recited in claim 12, wherein the second cavity is disposed between the drive surface of the spinal implant and the retention surface of the spinal implant.

14. A surgical system as recited in claim 13, wherein the second cavity includes a cone shaped cross section configured to align and direct the retention surface of the surgical instrument into engagement with the retention surface of the spinal implant.

15. A surgical system as recited in claim 13, wherein the gap has an angled surface configured to direct the surface of the surgical instrument into engagement with the retention surface.

16. A surgical system as recited in claim 12, wherein the drive surface of the spinal implant includes a hexalobe geometry configured for engagement with the drive surface of the surgical instrument.

17. A surgical system comprising:
 a driver including a drive surface and a retention surface; and
 a bone screw including threaded shaft and a head having a drive surface, a guide surface and a retention surface, the surfaces of the spinal implant defining a socket, the drive surface of the bone screw defining a first cavity of the socket, a guide surface defining a second cavity of the socket and the retention surface of the bone screw defining a third cavity of the socket, the surfaces of the bone screw being disposed in a serial configuration, the gap defining a maximum diameter of the socket;
 wherein at least one of the retention surfaces is tapered, and the retention surfaces are engageable to retain the bone screw with the driver.

18. A surgical system as recited in claim 17 wherein the gap has an angled surface configured to direct the retention surface of the driver into engagement with the retention surface of the bone screw.

19. A surgical system as recited in claim 17, wherein the retention surfaces are engageable to define a retention interface.

20. A spinal implant as recited in claim 17, wherein the retention surfaces form a friction fit.

* * * * *